(12) United States Patent
Goruganthu

(10) Patent No.: US 8,537,464 B2
(45) Date of Patent: Sep. 17, 2013

(54) OPTICAL ISOLATION MODULE AND METHOD FOR UTILIZING THE SAME

(75) Inventor: Rama R. Goruganthu, Austin, TX (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 853 days.

(21) Appl. No.: 12/653,235

(22) Filed: Dec. 9, 2009

(65) Prior Publication Data

US 2011/0134520 A1 Jun. 9, 2011

(51) Int. Cl.
*G02B 5/20* (2006.01)
*G02F 1/09* (2006.01)

(52) U.S. Cl.
CPC .................................... *G02F 1/093* (2013.01)
USPC ................................................... 359/484.03

(58) Field of Classification Search
None
See application file for complete search history.

(56) References Cited

U.S. PATENT DOCUMENTS 6,919,989 B1 * 7/2005 Deng et al. ............... 359/484.03

OTHER PUBLICATIONS

Ippolito, et al, *Angular spectrum tailoring in solid immersion microscopy for circuit analysis*. Applied Physics Letter 92, 101109 (2008).

* cited by examiner

*Primary Examiner* — Derek S Chapel
(74) *Attorney, Agent, or Firm* — Farjami & Farjami LLP

(57) ABSTRACT

According to one embodiment, an optical isolation module includes first and second linear polarizers, a Faraday rotator situated between the first and second linear polarizers and a transmissive element including a half-wave plate also situated between the first and second linear polarizers. In one embodiment, a method for performing optical isolation includes rotating an axis of polarization of a linearly polarized light beam by a first rotation in a first direction, and selectively rotating a portion of the linearly polarized light beam by a second rotation in the first direction to produce first and second linearly polarized light beam portions. As a result, the first linearly polarized light beam portion undergoes the first rotation, and the second linearly polarized light beam portion undergoes the first and second rotations. The method further includes filtering one of the first and second linearly polarized light beam portions to produce a light annulus.

13 Claims, 5 Drawing Sheets

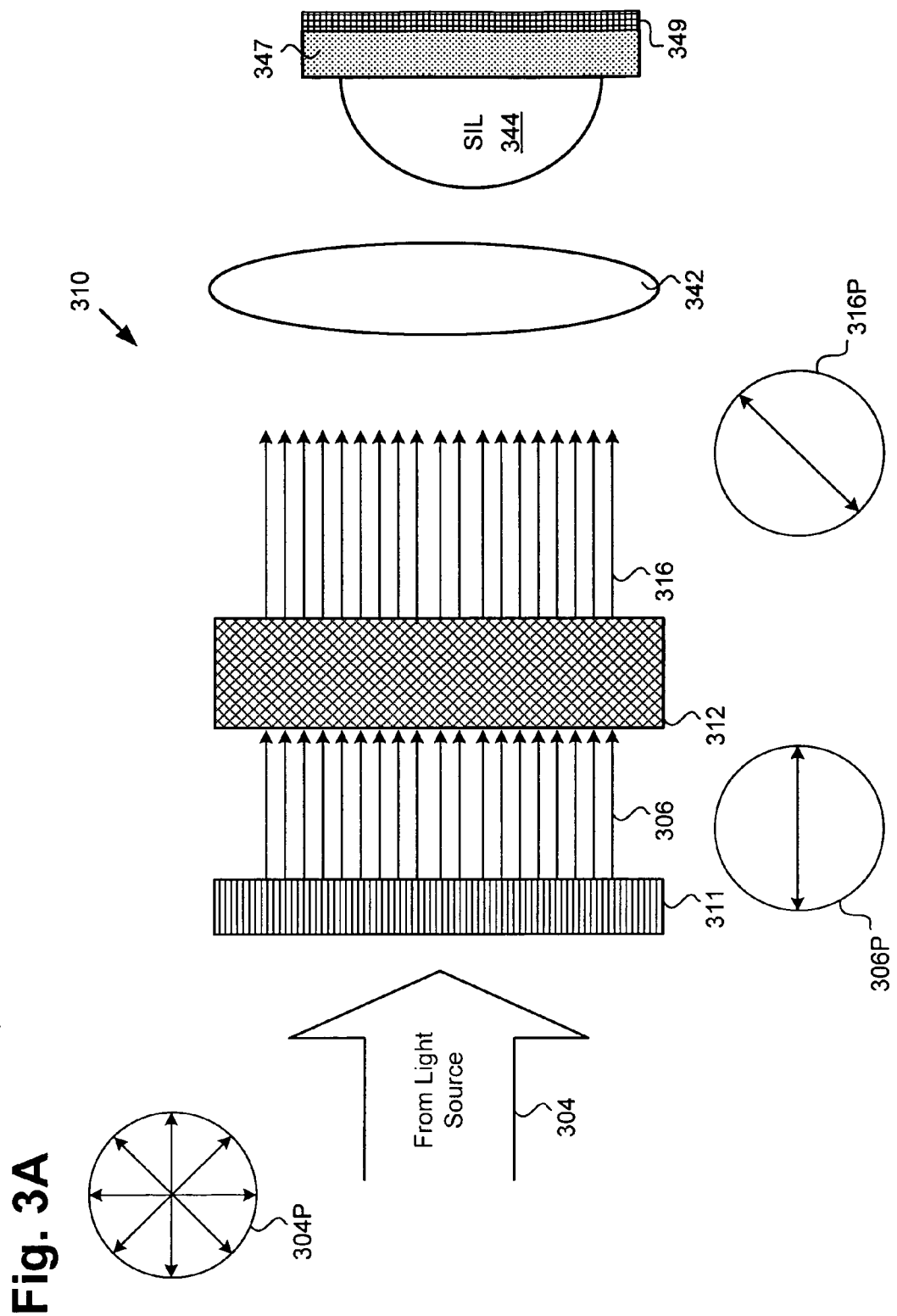

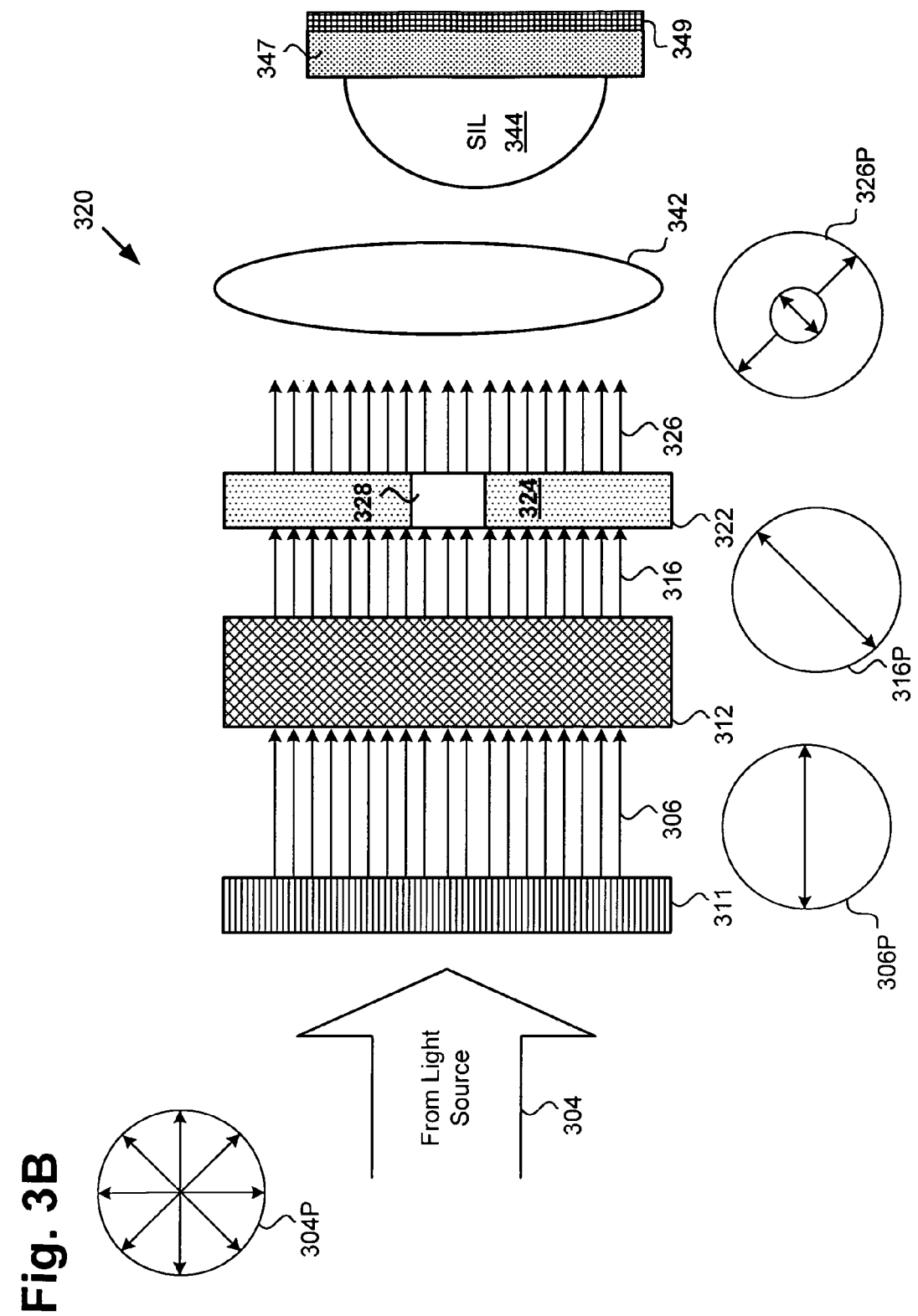

OPTICAL ISOLATION MODULE AND METHOD FOR UTILIZING THE SAME

BACKGROUND OF THE INVENTION

1. Field of the Invention

The present invention is generally in the field of fabrication of semiconductor devices. More particularly, the invention is in the field of imaging integrated circuits fabricated on a semiconductor wafer.

2. Background Art

Soft defect localization is a well known technique for detecting soft defects, such as timing marginalities, in fabricated semiconductor devices. Soft defect localization typically utilizes a laser to scan regions of a semiconductor device that is concurrently under test. Preferably, the laser is focused on a single transistor at a time to cause localized heating of that transistor as it is being tested. The laser light scattered from the transistor is then collected and analyzed, along with laser light scattered from other device features, to determine the locations of soft defects in the device. However, diffraction effects limit the resolution achievable using this approach. As the dimensions of modern integrated circuits become ever smaller, this traditional technique is no longer capable of isolating individual device features for soft defect analysis.

One conventional solution for performing soft defect analysis of high resolution semiconductor devices employs near field scanning optical microscopy (NSOM). In NSOM, an illuminated optical fiber is positioned very close to a surface being imaged, and is scanned across the surface in a tapping mode. Evanescent light from the tip of the optical fiber is scattered off of the surface, and is detected using a conventional microscope objective lens. Although NSOM has been shown to be effective for high resolution imaging, there are several significant drawbacks to its use in soft defect localization. For example, because the evanescent light from the tip decays very rapidly, only surface or near sub-surface structures can be imaged using the NSOM technique. In addition, scanning the optical fiber tip across the surface is a slow mechanical process, which additionally subjects the tip to erosion and breakage.

Thus, there is a need in the art for a robust high resolution imaging solution suitable for implementation in performing soft defect analysis of integrated circuits and devices.

SUMMARY OF EMBODIMENTS OF THE INVENTION

An optical isolation module and method for utilizing the same, substantially as shown in and/or described in connection with at least one of the figures, as set forth more completely in the claims. In one embodiment, an optical isolation module includes first and second linear polarizers, a Faraday rotator situated between the first and second linear polarizers and a transmissive element including a half-wave plate also situated between the first and second linear polarizers. A method for performing optical isolation using the optical isolation module includes rotating an axis of polarization of a linearly polarized light beam by a first rotation in a first direction, and selectively rotating a portion of the linearly polarized light beam by a second rotation in the first direction to produce first and second linearly polarized light beam portions. As a result, the first linearly polarized light beam portion undergoes the first rotation, and the second linearly polarized light beam portion undergoes the first and second rotations. The method can continue by filtering one of the first and second linearly polarized light beam portions to produce a light annulus.

BRIEF DESCRIPTION OF THE DRAWINGS

FIG. 3A is a block diagram showing the optical isolation module of FIG. 1 used in preliminary steps of the example method shown in FIG. 2, in accordance with one embodiment of the present invention.

FIG. 3B is a block diagram showing the optical isolation module of FIG. 1 used in an intermediate step of the example method shown in FIG. 2, in accordance with one embodiment of the present invention.

DETAILED DESCRIPTION OF EMBODIMENTS OF THE INVENTION

An embodiment of the present invention is directed to an optical isolation module and method for utilizing the same. The following description contains specific information pertaining to implementation(s) of the present invention. One skilled in the art will recognize that the present invention may be implemented in a manner different from that specifically discussed in the present application. Moreover, some of the specific details of the invention are not discussed in order not to obscure the invention.

The drawings in the present application and their accompanying detailed description are directed to merely exemplary embodiments of the invention. To maintain brevity, other embodiments of the present invention are not specifically described in the present application and are not specifically illustrated by the present drawings.

The present inventor has realized that high resolution imaging of semiconductor circuits and devices can be achieved through use of a dark field microscopy approach employing a solid immersion lens (SIL), in which light scattered from the target of the SIL along its central optical axis is collected by the microscopy system optics. In one example implementation, such an approach may be used to perform soft defect analysis of semiconductor devices residing on a wafer or die, for example.

In order for such an approach to achieve the imaging resolution required by the smallest device dimensions, the imaging light delivered to the SIL must be suitably manipulated to assure that the incident light is substantially comprised of supercritical light components undergoing total internal reflection within the wafer or die so as to produce evanescent fields within the semiconductor material. At the same time, it is desirable that the light scattered from the semiconductor wafer or die along or near the central axis of the SIL as a result of the supercritical imaging light incidence, be collected by the microscope optics. The present application discloses, amongst other aspects, a novel and inventive optical isolation module and method for its use that enables both delivery of substantially supercritical imaging light to a target semiconductor surface, as well as recovery of light scattered along or near an axis normal to that target surface.

Figure 1:
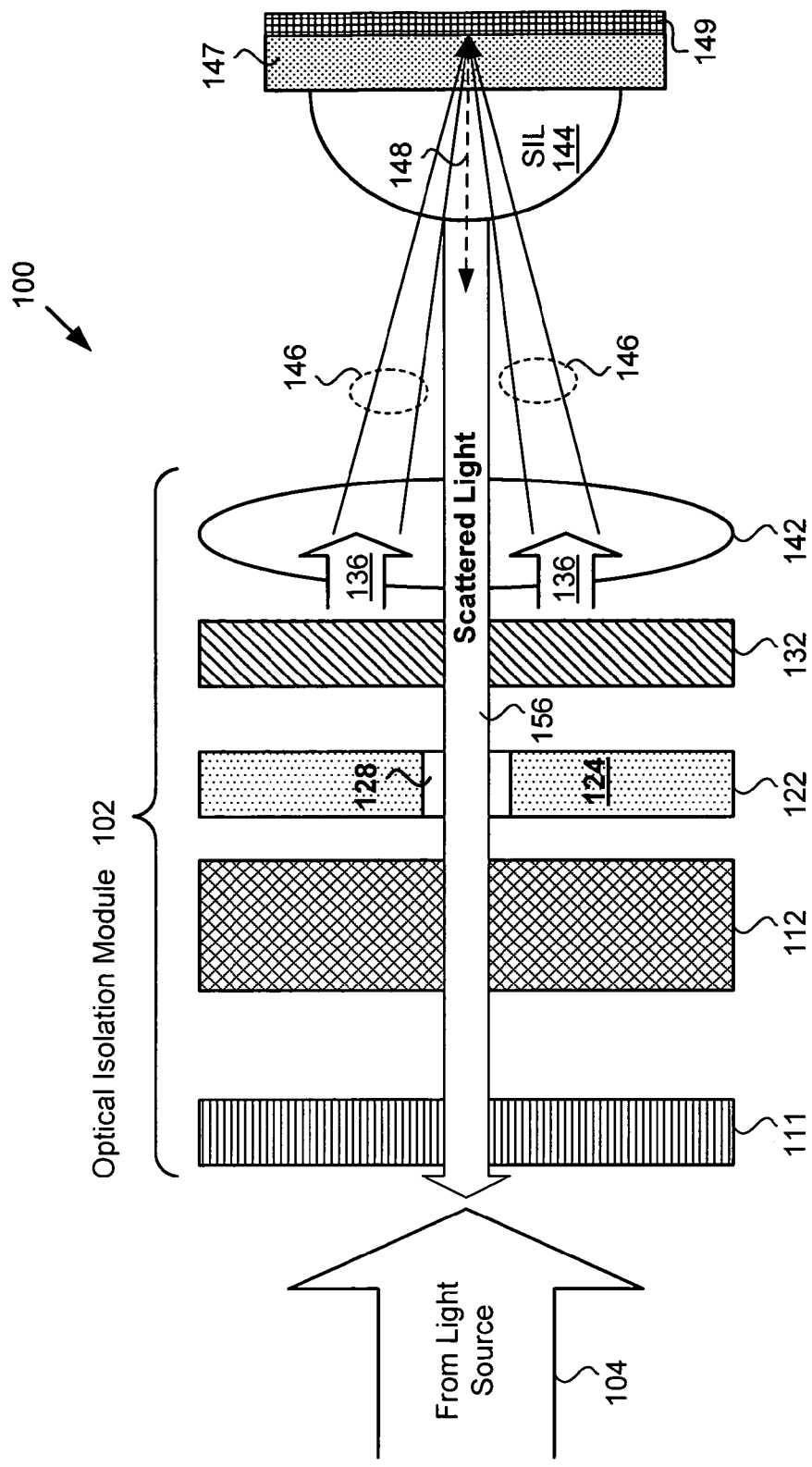
FIG. 1 is a block diagram of an integrated circuit imaging arrangement including an optical isolation module in accordance with one embodiment of the present invention.

FIG. 1 is a block diagram of integrated circuit (IC) imaging arrangement 100 including optical isolation module 102 in accordance with one embodiment of the present invention. Imaging arrangement 100 includes imaging light 104, optical isolation module 102, SIL 144, and scattered light 156 collected from a target surface investigated by SIL 144, such as the backside of semiconductor wafer or die 147, for example, on which circuit 149 is fabricated. Imaging arrangement 100 may be implemented in a laser scanning microscopy system to perform soft defect analysis of semiconductor devices fabricated below the target surface, for example, using a dark field microscopy approach.

According to the embodiment of FIG. 1, imaging light 104 is received from a light source of the optical microscopy system (also not shown in FIG. 1), such as a laser source, for example, enters optical isolation module 102 at first linear polarizer 111, and exits optical isolation module 102 as substantially supercritical incident rays 146. Incident rays 146 are provided to SIL 144 for use in imaging semiconductor devices of circuit 149. Scattered light 156 from circuit 149 and traveling along or near central optical axis 148 of SIL 144 can then be collected through optical isolation module 102 for use in imaging the semiconductor devices.

As will be explained below in greater detail, optical isolation module 102 is configured to receive imaging light 104, to produce annulus of imaging light 136 shaped so as to provide substantially supercritical incident rays 146 while concurrently blocking subcritical imaging light components, and to collect scattered light 156 along central optical axis 148 of SIL 144. Optical isolation module 102 comprises first linear polarizer 111, which is represented in the present embodiment as a horizontal polarizer, second linear polarizer 132, Faraday rotator 112, and transmissive element 122 including half-wave plate 124 and aperture 128. According to the embodiment of optical isolation module 102 shown in FIG. 1, Faraday rotator 112 and transmissive element 122 are situated between first linear polarizer 111 and second linear polarizer 132. In addition, optical isolation module 102 is shown to comprise microscope objective lens 142, which is optionally included in an optical isolation module according to the present inventive concepts.

It is noted that although FIG. 1 shows optical isolation module 102 as comprising particular elements in a particular order, in other embodiments, optical isolation module 102 may or may not include microscope objective lens 142, and may have an arrangement other than that shown in FIG. 1. Thus, for example, in some embodiments, microscope objective lens 142, while retaining a role in an imaging arrangement such as imaging arrangement 100, may be omitted from optical isolation module 102. In embodiments in which it is included in optical isolation module 102, microscope objective lens 142 may be situated as shown in FIG. 1, or may be situated between first linear polarizer 111 and second linear polarizer 132. Moreover, although the embodiment of FIG. 1 represents Faraday rotator 112 as being situated between first linear polarizer 111 and transmissive element 122, in other embodiments, transmissive element 122 may be interposed between first linear polarizer 111 and Faraday rotator 112.

It is further noted that the particular implementational environment represented in the present figures is shown for conceptual clarity, and is not to be interpreted as a limitation. As shown and discussed herein, the present inventive concepts have applicability to high resolution imaging of semiconductor devices. More generally, however, the present invention may be utilized to enable laser scanning microscopy on nanomaterials and biological samples, as well as semiconductor dies, either packaged or on wafer.

Figure 2:
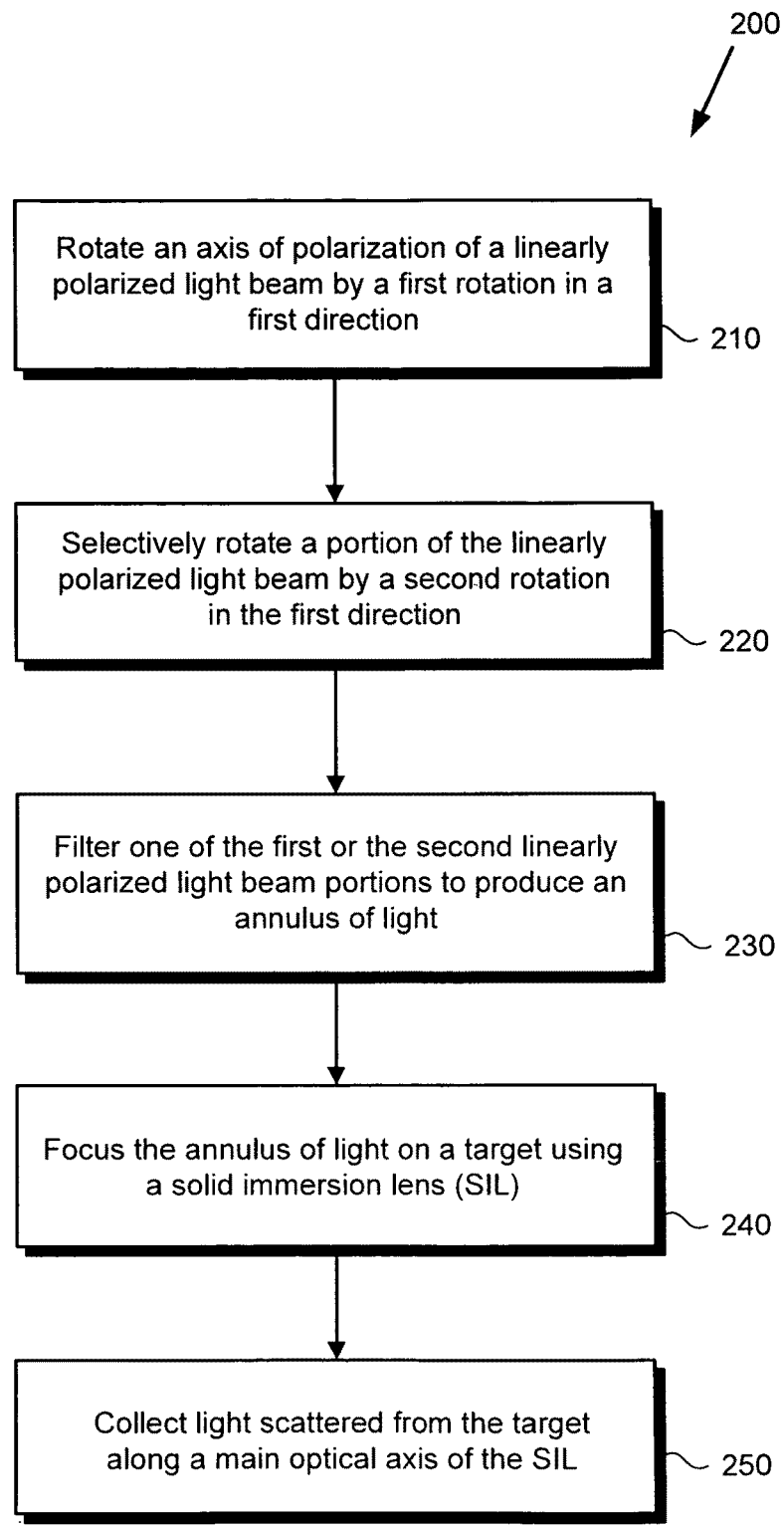
FIG. 2 is a flowchart presenting a method for performing optical isolation, in accordance with one embodiment of the present invention.

The advantageous features of optical isolation module 102 will now be further disclosed in conjunction with FIGS. 2, 3A, 3B, and 3C. FIG. 2 presents flowchart 200 describing a method for performing optical isolation, according to one embodiment of the present invention. Certain details and features have been left out of flowchart 200 that are apparent to a person of ordinary skill in the art. For example, a given step may consist of one or more substeps or may involve specialized equipment or materials, as known in the art. While steps 210 through 250 indicated in flowchart 200 are sufficient to describe some embodiments of the present method, other embodiments may utilize steps different from those shown in flowchart 200, or may include more, or fewer steps.

Figure 3C:
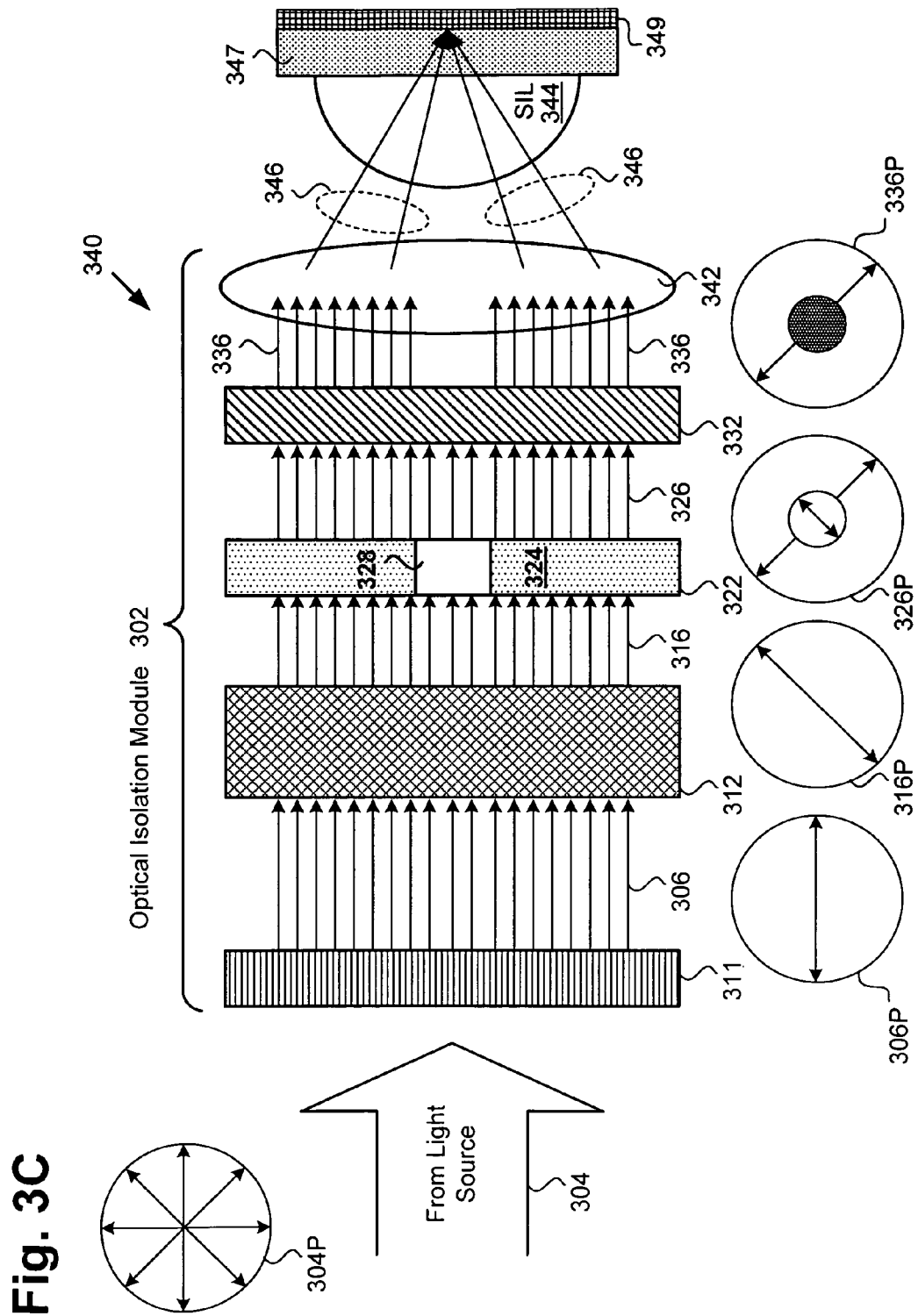
FIG. 3C is a block diagram showing the optical isolation module of FIG. 1 used in another intermediate step of the example method shown in FIG. 2, in accordance with one embodiment of the present invention.

Turning now to FIG. 3A, imaging arrangement 310 of FIG. 3A shows elements of optical isolation module 102, in FIG. 1, used in preliminary steps of the example method of flowchart 200, in FIG. 2. Imaging arrangement 310 shows imaging light 304, first linear polarizer 311, Faraday rotator 312, microscope objective lens 342, SIL 344, semiconductor wafer or die 347, and circuit 349, corresponding respectively to imaging light 104, first linear polarizer 111, Faraday rotator 112, microscope objective lens 142, SIL 144, semiconductor wafer or die 147, and circuit 149, in FIG. 1. Also shown in FIG. 3A is polarization diagram 304P of imaging light 304, as well as linearly polarized light 306, first rotated imaging light 316, and their respective polarization diagrams 306P and 316P. Referring to FIGS. 3B and 3C, imaging arrangements 320 and 340 show the result of performing, on imaging light 304, steps 220 and 240 of flowchart 200 of FIG. 2, respectively, by various elements of optical isolation module 302, shown in FIG. 3C and corresponding to optical isolation module 102, in FIG. 1. Thus, for example, imaging arrangement 310 shows the changes produced in imaging light 304, as a result of optical isolation module 302 performing step 210 of flowchart 200, while imaging arrangements 320 and 340 show imaging light 304 following respective optical isolation steps 220 and 240 performed by optical isolation module 302.

Beginning with step 210 in FIG. 2 and referring to FIGS. 3A and 3C, step 210 of flowchart 200 comprises rotating the axis of polarization of a linearly polarized light beam in a first direction. Step 210 may be performed by optical isolation module 302, in FIG. 3C, for example. Referring to FIG. 3A, step 210 corresponds to a forty-five degree (45°) anti-clockwise rotation of the axis of polarization of linearly polarized light 306, by Faraday rotator 312, to first rotated imaging light 316.

As shown by polarization diagram 304P, it is contemplated that imaging light 304 may arrive at the optical isolation module in an unpolarized state. First linear polarizer 311, which is represented as a horizontal polarizer, passes linearly polarized light 306 having a horizontal axis of polarization into optical isolation module 302, as shown by polarization diagram 306P. As further shown by polarization diagram 316P, step 210 imposes a 45° anti-clockwise rotation on linearly polarized light 306 passed by first linear polarizer 311. Although the embodiment of FIG. 3A represents first linear polarizer 311 as a horizontal polarizer, that characterization is merely exemplary. In other embodiments, first linear polarizer 311 may impose an axis of polarization having any angular deflection on imaging light 304. Moreover, because linearly polarized light 306 may have an angle of polarization other than zero degrees (0°), i.e., polarized light 306 may not be horizontally polarized, the 45° anti-clockwise rotation imposed on linearly polarized light 306 by Faraday rotator 312 may result in first rotated imaging light 316 having a polarization other than that shown by polarization diagram 316P.

Continuing with step 220 in FIG. 2, and referring to FIGS. 3B and 3C, step 220 of flowchart 200 comprises selectively rotating a portion of the linearly polarized light beam by a second rotation in the first direction. Step 220 may be performed by transmissive element 322 of optical isolation module 302. As previously noted, transmissive element 322 includes half-wave plate 324. In the present embodiment, that arrangement is represented by annular half-wave plate 324 (shown in cross-section in FIG. 3B) surrounding central aperture 328 of transmissive element 322, which may comprise a circular aperture having a diameter of approximately 2.3 mm, for example. As a result, the portion of first rotated imaging light 316 passing through half-wave plate 324 is rotated an additional ninety degrees (90°) in the anti-clockwise direction, while the portion passing through aperture 328 is not further rotated. Thus, step 220 imposes a selective rotation on a portion of linearly polarized and first rotated imaging light 316 to produce optically isolated imaging light 326 comprising a first linearly polarized light beam portion, e.g., the portion passing through aperture 328 of transmissive element 322 and having undergone only the first rotation imposed by Faraday rotator 112, and a second linearly polarized light beam portion, e.g., the portion passing through half-wave plate 324 of transmissive element 322 and having undergone a second 90° rotation in the same direction as the 45° first rotation imposed by Faraday rotator 312.

Consequently, as shown by polarization diagram 326P, optically isolated imaging light 326 passing through transmissive element 322 is characterized by an annular portion having an axis of polarization perpendicular to the axis of polarization of its central portion. As further shown by polarization diagram 326P, according to the present embodiment, steps 210 and 220 result in an annular light beam portion having passed through half-wave plate 324 and having an axis of polarization rotated by one hundred thirty-five degrees (135°) anti-clockwise, and a central light beam portion having passed through aperture 328 and having an axis of polarization rotated by 45° anti-clockwise.

Moving on to step 230 of FIG. 2, and referring to FIG. 3C, step 230 of flowchart 200 comprises filtering one of the first and second linearly polarized light beam portions resulting from step 220, to produce annulus of imaging light 336. According to the embodiment of FIG. 3C, step 230 corresponds to filtering optically isolated light imaging 326, having two linearly polarized portions with their respective axes of polarization perpendicular to one another, using second linear polarizer 332 having its axis of polarization selected to transmit the annular light beam portion. Because the axis of polarization of the central light beam portion is perpendicular to that of the annular portion, it is also substantially perpendicular to the polarization axis of second linear polarizer 332, causing the central portion of the polarized light beam to be blocked.

Thus, according to the present embodiment, second linear polarizer 332 has its axis of polarization set at 135°, thereby substantially passing annulus of imaging light 336, as shown by polarization diagram 336P, in which the central section is represented as dark to indicate blockage of the central portion of optically isolated imaging light 326 by second linear polarizer 332. Although the foregoing discussion of various components of optical isolation module 302 describes one possible implementational model, there are numerous variations. For example, exchanging the locations of Faraday rotator 312 and transmissive element 322 would produce substantially the same cumulative rotation of the respective first and second portions of optically isolated imaging light 326, as is achieved by the embodiment of FIG. 3C.

Moreover, in another embodiment, transmissive element 322 may have its central section 328 occupied by a half-wave plate, the annular region 324 being configured so as to impose substantially no rotation on the transmitted light. In that embodiment, annular portion of optically isolated imaging light 326 would undergo a single rotation of 45°, due to passage through Faraday rotator 312, while the central portion of optically isolated imaging light 336 would be rotated twice, producing a cumulative rotation of 135° for that central portion. Simple substitution of second linear polarizer 332 with a linear polarizer having its polarization axis set to 45°, rather than 135°, would once again substantially transmit annulus of imaging light 336 while substantially blocking the central portion of optically isolated imaging light 326.

Continuing with step 240 of FIG. 2, and continuing to refer to FIG. 3C, step 240 of flowchart 200 comprises focusing annulus of imaging light 336 on a target, such as circuit 349 fabricated on semiconductor wafer or die 347, using SIL 344. Step 240 corresponds to SIL 344 receiving substantially supercritical incident rays 346 from optical isolation module 302 through microscope objective lens 342. As a result, SIL 344 may be utilized to image individual devices in circuit 349 using the supercritical imaging light provided by optical isolation module 302.

Moving to step 250 of FIG. 2, and referring back to FIG. 1, step 250 of flowchart 200 comprises collecting light scattered from circuit 149 along central optical axis 148 of SIL 144. By way of example, we invoke the sample implementational details ascribed to the embodiment shown by FIGS. 3A through 3C. That is to say, let us assume that first linear polarizer 111 is a horizontal polarizer, transmissive element 122 includes annular half-wave plate 124 and aperture 128, and that the polarization axis of second linear polarizer 132 is selected so as to pass annulus of imaging light 136 to SIL 144.

In that implementational setting, scattered light 156 directed along central optical axis 148 of SIL 144 (near-axis scattered light) is polarized by second linear polarizer 132, passes substantially unaltered through aperture 128 of transmissive element 122, and is rotated by 45° in a clockwise direction by Faraday rotator 112. As a result, scattered light 156 encounters first linear polarizer 111 as horizontally polarized light and is substantially passed to a detector of the imaging system as a result (detector not shown in FIG. 1). The described clockwise rotation of scattered light 156 is the result of the unique properties of a Faraday rotator, in which the direction of rotation produced by the Faraday rotator changes according to the direction of light propagation through the Faraday rotator, as is known in the art. Thus, including Faraday rotator 112 as a component of optical isolation module 102 results in anti-clockwise rotation of linearly polarized imaging light traveling towards SIL 144, but clockwise rotation of scattered light 156 traveling away from SIL 144, enabling collection of scattered light 156 in step 250.

More generally, step 250 corresponds to linearly polarizing scattered light 156, e.g., by second linear polarizer 132, and selectively rotating a portion of the linearly polarized scattered light by a third rotation in the first direction to produce first and second linearly polarized scattered light portions. In other words, the off-axis portions of the scattered light (off-axis scattered light not shown in FIG. 1) passing through half-wave plate 124 are rotated 90° anti-clockwise, while the near-axis scattered light, e.g., scattered light 156, is not rotated during passage through aperture 128. Step 250 further comprises rotating the first and second linearly polarized scattered light portions in a second direction opposite the first direction by a fourth rotation, e.g., 45° clockwise rotation of both the off-axis scattered light and near-axis scattered light 156. As a result, near-axis scattered light 156 undergoes only the fourth rotation, while the off-axis scattered light portion undergoes both the third and fourth rotations. Subsequent filtering by first linear polarizer 111 results in blockage of the off-axis scattered light and allows passage and collection of near-axis scattered light 156 traveling along central optical axis 148.

More generally still, although the present scattered light collection step 250 has been described in terms of specific design parameters, consideration of the implementational variations discussed above reveals that the all of the various embodiments of optical isolation module 102 described herein can be configured to (1) deliver annulus of imaging light 136 comprising substantially supercritical components while concurrently substantially blocking subcritical imaging light components, and (2) collect near-axis scattered light 156 traveling along central optical axis 148 of SIL 144.

The present inventor has realized that a substantial portion of the light scattered from a target semiconductor device as a result of the evanescent fields produced in a wafer or die by imaging arrangement 100 is directed along central optical axis 148. As a result, significant advantages accrue from providing a solution capable of both blocking a subcritical central portion of an imaging light beam along a central optical axis in order to deliver substantially supercritical imaging light to the target device, and of collecting scattered light 156 along the central optical axis to enhance image brightness and contrast.

By contrast, conventional approaches to producing an annulus of supercritical imaging light, such as annulus of imaging light 136, do so by implementing an opaque light stop to block the central portion containing subcritical light components. However, that conventional approach constrains collection of scattered light, because the same light stop prevents collection of scattered light along the central optical axis. As discussed above, the present application discloses a solution that desirably enables the delivery of substantially supercritical imaging light components, the blocking of substantially subcritical imaging light components, and the highly advantageous collection of scattered light along a central optical axis of a SIL.

Consequently, the present approach discloses a solution capable of achieving imaging resolutions comparable to those achieved using near field scanning optical microscopy (NSOM). Like the NSOM approach, the spatial resolution achievable by embodiments of the present invention are not limited by diffraction. As a result, embodiments of the present invention can provide lateral resolution on the order fifty nanometers (50 nm). However, unlike NSOM, the present inventive concepts can be advantageously used with thermal solutions such as spray cooling. Moreover, whereas NSOM is limited to surface and near surface imaging only, the present solution is compatible with substrate silicon thicknesses between approximately ninety micrometers and approximately one hundred ten micrometers (approximately 90 μm to approximately 110 μm).

In addition, unlike NSOM, in which imaging is performed in a purely mechanical tapping mode, the present approach lends itself to implementation in a laser scanning microscopy system capable of rapidly and efficiently imaging devices fabricated on a semiconductor wafer or die. Furthermore, because embodiments of the present invention can be implemented in combination with a SIL, rather than the delicate optical tip used in NSOM to scan a target surface, the disclosed solution represents a more robust approach to IC and device imaging, and for circuit analysis applications such as soft defect localization.

From the above description of the invention it is manifest that various techniques can be used for implementing the concepts of the present invention without departing from its scope. Moreover, while the invention has been described with specific reference to certain embodiments, a person of ordinary skill in the art would appreciate that changes can be made in form and detail without departing from the spirit and the scope of the invention. Thus, the described embodiments are to be considered in all respects as illustrative and not restrictive. It should also be understood that the invention is not limited to the particular embodiments described herein but is capable of many rearrangements, modifications, and substitutions without departing from the scope of the invention.

The invention claimed is:

1. An optical isolation module comprising:
   first and second linear polarizers;
   a Faraday rotator situated between said first and second linear polarizers; and
   a transmissive element including an aperture and a half-wave plate, said transmissive element situated between said first and second linear polarizers.

2. The optical isolation module of claim 1, wherein said transmissive element is situated between said second linear polarizer and said Faraday rotator.

3. The optical isolation module of claim 1, wherein said optical isolation module is implemented in combination with a solid immersion lens (SIL).

4. The optical isolation module of claim 3, wherein said optical isolation module is configured to collect light scattered along a central optical axis of said SIL.

5. The optical isolation module of claim 3, further comprising a microscope objective lens situated between said second linear polarizer and said SIL.

6. A method for performing optical isolation, said method comprising:
   rotating an axis of polarization of a linearly polarized light beam by a first rotation in a first direction;
   selectively rotating a portion of said linearly polarized light beam by a second rotation in said first direction to produce first and second linearly polarized light beam portions, said first linearly polarized light beam portion having undergone said first rotation and said second linearly polarized light beam portion having undergone said first and second rotations; and
   filtering one of said first and second linearly polarized light beam portions to produce a light annulus from said light beam.

7. The method of claim 6, wherein said method is performed by an optical isolation module, said optical isolation module comprising:
   first and second linear polarizers;
   a Faraday rotator situated between said first and second linear polarizers; and
   a transmissive element including a half-wave plate, said transmissive element situated between said first and second linear polarizers.

8. The method of claim 7, wherein said transmissive element of said optical isolation module is situated between said second linear polarizer and said Faraday rotator of said optical isolation module.

9. The method of claim 6, further comprising focusing said light annulus on a target by a solid immersion lens (SIL).

10. The method of claim 9, further comprising collecting a scattered light from said target along a central optical axis of said SIL.

11. The method of claim 10, wherein said collecting said scattered light along said central optical axis of said SIL comprises:

linearly polarizing said scattered light;

selectively rotating a portion of said linearly polarized scattered light by a third rotation in said first direction to produce first and second linearly polarized scattered light portions;

rotating said first and second linearly polarized scattered light portions in a second direction opposite said first direction by a fourth rotation, said first linearly polarized scattered light portion having undergone said fourth rotation and said second linearly polarized scattered light portion having undergone said third and fourth rotations; and filtering one of said first and second linearly polarized scattered light portions to collect said scattered light along said central optical axis of said SIL.

12. The method of claim 11, wherein said method is performed by an optical isolation module, said optical isolation module comprising:

first and second linear polarizers;

a Faraday rotator situated between said first and second linear polarizers; and a transmissive element including a half-wave plate, said transmissive element situated between said first and second linear polarizers.

13. The method of claim 12, wherein said transmissive element of said optical isolation module is situated between said second linear polarizer and said Faraday rotator of said optical isolation module.

* * * * *